United States Patent
Cutillo et al.

(10) Patent No.: US 11,324,690 B2
(45) Date of Patent: May 10, 2022

(54) COMPOSITION FOR RESTORATIVE VAGINAL LUBRICATION AND A METHOD OF USE THEREOF

(71) Applicants: Dawn Marie Cutillo, Ephrata, PA (US); Kyle Holderman, Valley Center, CA (US)

(72) Inventors: Dawn Marie Cutillo, Ephrata, PA (US); Kyle Holderman, Valley Center, CA (US)

(*) Notice: Subject to any disclaimer, the term of this patent is extended or adjusted under 35 U.S.C. 154(b) by 241 days.

(21) Appl. No.: 16/847,392

(22) Filed: Apr. 13, 2020

(65) Prior Publication Data
US 2021/0007968 A1    Jan. 14, 2021

Related U.S. Application Data

(60) Provisional application No. 62/804,584, filed on Feb. 12, 2019.

(51) Int. Cl.
| | |
|---|---|
| *A61K 8/9789* | (2017.01) |
| *A61K 8/34* | (2006.01) |
| *A61K 8/37* | (2006.01) |
| *A61K 8/92* | (2006.01) |
| *A61K 8/55* | (2006.01) |
| *A61K 8/73* | (2006.01) |
| *A61K 8/365* | (2006.01) |
| *A61K 8/36* | (2006.01) |
| *A61K 8/63* | (2006.01) |
| *A61K 8/368* | (2006.01) |
| *A61Q 19/00* | (2006.01) |

(52) U.S. Cl.
CPC ............ *A61K 8/9789* (2017.08); *A61K 8/342* (2013.01); *A61K 8/345* (2013.01); *A61K 8/36* (2013.01); *A61K 8/365* (2013.01); *A61K 8/368* (2013.01); *A61K 8/37* (2013.01); *A61K 8/553* (2013.01); *A61K 8/63* (2013.01); *A61K 8/73* (2013.01); *A61K 8/92* (2013.01); *A61Q 19/007* (2013.01)

(58) Field of Classification Search
None
See application file for complete search history.

(56) References Cited

U.S. PATENT DOCUMENTS

| | | | |
|---|---|---|---|
| 4,542,129 A | 9/1985 | Orentreich | |
| 5,877,216 A * | 3/1999 | Place | A61K 9/0034 514/573 |
| 2003/0165547 A1 | 9/2003 | Picard-Lesboueyries et al. | |
| 2007/0292493 A1 | 12/2007 | Brierre | |
| 2015/0313949 A1 | 11/2015 | Cutillo | |

FOREIGN PATENT DOCUMENTS

| | | |
|---|---|---|
| JP | S629577 B2 | 2/1987 |
| WO | WO1997003676 A1 | 2/1997 |

* cited by examiner

*Primary Examiner* — Dominic Lazaro

(57) ABSTRACT

A composition for restorative vaginal lubrication and a method of use thereof facilitates enhances the overall vaginal health. The composition includes a quantity of water, a quantity of glycerin, a quantity of cetearyl alcohol, a quantity of glyceryl stearate, a quantity of avocado oil, a quantity of squalene oil, a quantity of lecithin, a quantity of benzoin oil, a quantity of xanthan gum, a quantity of citric acid, a quantity of potassium sorbate, a quantity of Dehydroepiandrosterone (DHEA), a quantity of elderberry extract, a quantity of damiana extract, a quantity of progesterone, a quantity of pomegranate oil, and a quantity of sodium benzoate. The composition is homogeneously mixed into a vaginal salve that may be both externally and internally applied with the vaginal area in order to moisturize the vaginal area and enhance sexual pleasure during sexual activity. The vaginal salve also promotes blood circulation for the vaginal area.

18 Claims, 3 Drawing Sheets

Vaginal Salve

- Water
- Cetearyl Alcohol
- Glyceryl Stearate
- Xanthan Gum
- Citric Acid
- Potassium Sorbate
- Elderberry Extract
- Damiana Extract
- Sodium Benzoate
- Glycerin
- Avocado Oil
- Squalene Oil
- Lecithin
- Benzoin Oil
- Dehydroepiandrosterone
- Progesterone
- Pomegranate Oil

FIG. 1

COMPOSITION FOR RESTORATIVE VAGINAL LUBRICATION AND A METHOD OF USE THEREOF

The current application claims a priority to the U.S. provisional patent application Ser. No. 62/804,584 filed on Feb. 12, 2019. The U.S. provisional patent application 62/804,584 is revived within the two-month period for unintentional abandonment on Apr. 13, 2020, while Apr. 12, 2020 was on a weekend.

FIELD OF THE INVENTION

The present invention generally relates to compositions for vaginal lubrication and moisturizer. More specifically, the present invention produces a quantity of vaginal salve that lubricates, promotes blood circulation, maintains vaginal pH, and maintains the integrity of vaginal walls.

BACKGROUND OF THE INVENTION

Myths about estrogen and the effects of estrogen for vaginal area limit sexual health and overall vaginal health. Although estrogen temporarily increases circulation to a cell, estrogen also increases oxygen demand in that cell causing an oxygen deficit. The plumping effect that estrogen gives to cells is simply water retention due to the stress the cell is under. This stress starts the cell division process associated with some of the dangers of estrogen. Estrogen causes the cross-linking of collagen which actually hardens and stiffens cells over time. Effects of estrogen on ligaments have shown to have a weakening effect which can lead to prolapse of the organs of the pelvic floor leading to incontinence and pain, all interfering.

The present invention is a trans-dermal vaginal cream to aid women who suffer from vagina dryness. The present invention is a non-estrogen vaginal cream that makes the present invention safe and usable by even women who fear estrogen related cancers. The present invention is applied a few times a week to start via a small vaginal applicator, then as the condition improves, the present invention can be applied weekly or by-weekly. The present invention also serves a lubricator during sexual activity and is non-condom safe due to its oil content. The present invention is designed to be both a sexual lubricant and moisturizer. The present invention includes natural ingredients in a natural base to avoid many of the synthetic ingredients that are harmful and easily absorbed through this delicate tissue area. The present invention does not include synthetic ingredients like petroleum-based ingredients, silicone-based ingredients, parabens, phenoxyethanol, propylene glycol, glycerin, chlorhexidine, etc. The present invention lasts longer without reapplication, providing more lubrication and slide due to the consistency compared to other sexual lubricants that are water or silicone based. The present invention is meant to accomplish vaginal rejuvenating without the use of estrogen which is believed to be beneficial for vaginal walls.

BRIEF DESCRIPTION OF THE DRAWINGS

FIG. 1 is a block diagram of the present invention.

DETAIL DESCRIPTIONS OF THE INVENTION

Figure 2:
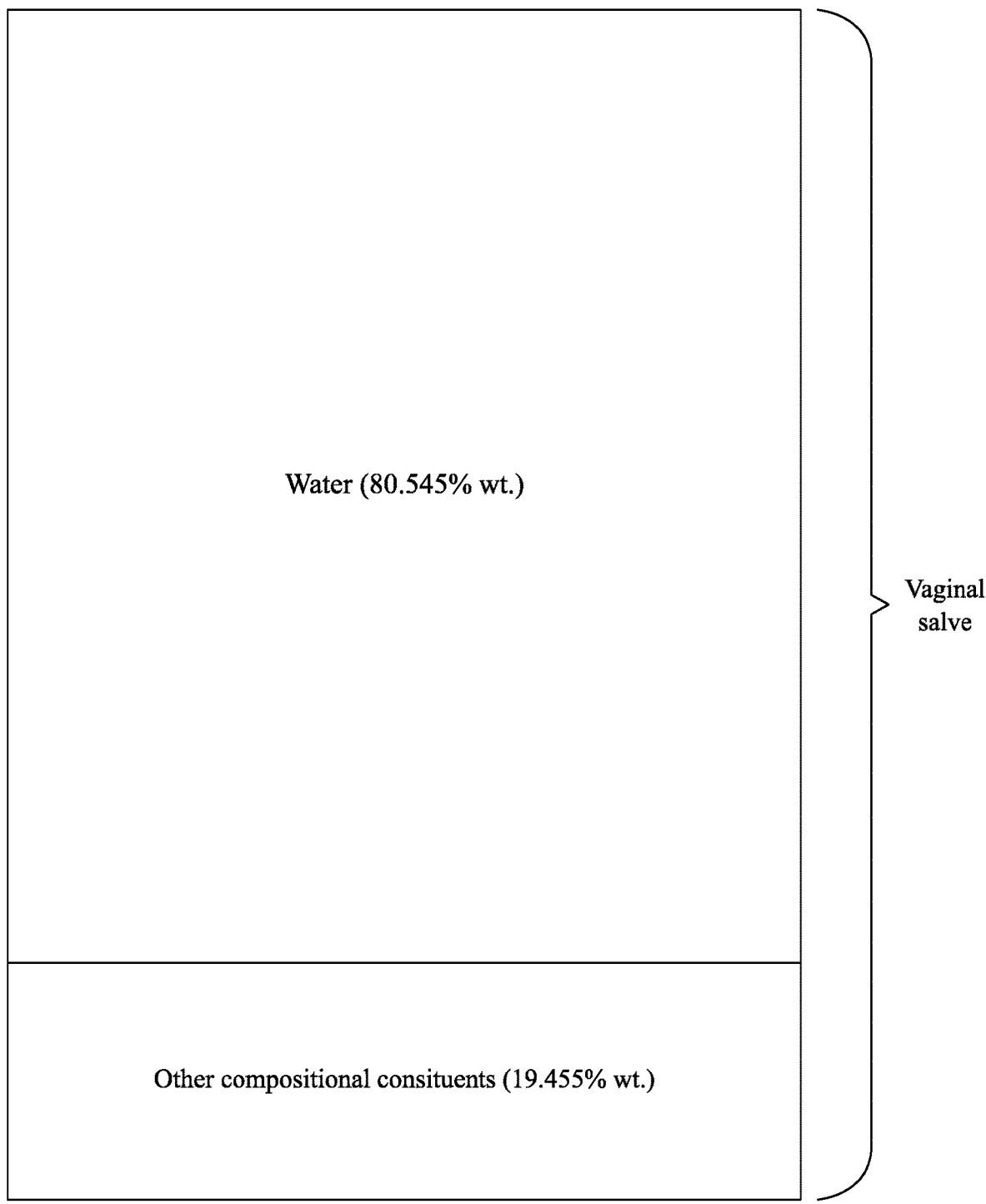
FIG. 2 is a block diagram illustrating the proportions of the present invention.

All illustrations of the drawings are for the purpose of describing selected versions of the present invention and are not intended to limit the scope of the present invention.

The present invention is a composition for a restorative vaginal lubrication and a method and use thereof. The present invention increases the amount of time for sexual activity and serves as a lubricant for increased performance. Moreover, the present invention is a natural lubricant that avoids any chemical or toxic ingredients, reducing or eliminating any possible allergies. The present invention is both nicely and naturally scented and serves as an aphrodisiac as well, further enhancing sexual activity. Sexual pleasure is enhanced as the present invention increases circulation to the sexual organs, such as the clitoris and the vaginal walls during sexual activity. More specifically, the present invention helps women suffering from vaginal atrophy and pelvic organ prolapse. The present invention reduces the amount of yeast infections and bacterial infections as a result of imbalanced pH levels, either from sexual activity or vaginal health. The present invention maintains vaginal health between sexual intercourse whether it is multiple days between sexual intercourse or a day between sexual intercourse. Hormone levels are also maintained with the application of the present invention in order to balance out estrogen dominance. Moisture of the vaginal area is also maintained for a day-to-day basis or for sexual activity. As seen in FIG. 1, the composition of the restorative vaginal lubrication comprises a quantity of water, a quantity of glycerin, a quantity of cetearyl alcohol, a quantity of glyceryl stearate, a quantity of avocado oil, a quantity of squalene oil, a quantity of lecithin, a quantity of benzoin oil, a quantity of xanthan gum, a quantity of citric acid, a quantity of potassium sorbate, a quantity of Dehydroepiandrosterone (DHEA), a quantity of elderberry extract, a quantity of damiana extract, a quantity of progesterone, a quantity of pomegranate oil, and a quantity of sodium benzoate. Thus, the quantity of water, the quantity of glycerin, the quantity of cetearyl alcohol, the quantity of glyceryl stearate, the quantity of avocado oil, the quantity of squalene oil, the quantity of lecithin, the quantity of benzoin oil, the quantity of xanthan gum, the quantity of citric acid, the quantity of potassium sorbate, the quantity of DHEA, the quantity of elderberry extract, the quantity of damiana extract, the quantity of progesterone, the quantity of pomegranate oil, and the quantity of sodium benzoate are homogeneously mixed into a vaginal salve.

The vaginal salve is an oil in water emulsion, with the quantity of avocado oil and the quantity of pomegranate oil as a base. The vaginal salve serves as a vaginal rejuvenation as the quantity of DHEA and the quantity of progesterone are integrated in an encapsulated liposome delivery system allowing the vaginal salve to serve as a true transdermal delivery system. The vaginal salve penetrates through the epidermis of the skin of the vulva or the vaginal mucosa. The quantity of damiana extract aids the absorption and utilization of the quantity of DHEA and the quantity of progesterone. As the vaginal salve is a transdermal delivery system, any excess amount of the vaginal salve applied is urinated out, and there is no overapplication of the vaginal salve. More specifically, any excess of the quantity of DHEA and the quantity of progesterone is urinated out so that only necessary amount of the quantity DHEA and the quantity of progesterone is absorbed into the body to help balance estrogen dominance. The quantity of squalene oil is a solvent that carries and combines non-encapsulated active ingredients into the lipid barrier of the epidermal cells and on to the blood stream. The quantity of DHEA and the quantity of progesterone act in a similar manner by mimicking the solubility of the epidermal lipids and passing through to the blood stream. The quantity of DHEA and the quantity of progesterone contain some of the active ingredients which are liberated as the micelles break down and release the contents. The two delivery strategies function synergistically to act as a time release mechanism. Therefore, vaginal rejuvenation occurs when a woman is sleeping.

The vaginal salve serves as an aphrodisiac to promote sexual activity and therefore forms a conditioned response whenever applied. The quantity of benzoin is an essential oil that facilitates a sexual arousal between individuals. The aphrodisiac qualities are further enhancing with the quantity of damiana extract. The quantity of damiana extract is from the damiana herb that enhances female sexual function and reduces vaginal dryness. The quantity of damiana extract also increases circulation to the topical cells of the vulva and vaginal walls. With increased circulation, the quantity of DHEA and the quantity of progesterone can be carried via the bloodstream deeper into the other layers of cells of these areas. Furthermore, increased circulation across the vaginal walls keeps the vaginal area healthy and provides moisture during and in between sexual activity.

The vaginal salve further enhances sexual pleasure as the nerves associated with the vagina, including the clitoris and vaginal lips, are healthier and increased blood circulation across the vaginal area with the application of the vaginal salve. The quantity of progesterone keeps these nerves healthy, which is essential to proper orgasming. The vaginal salve also reinforces the thickness and integrity of the sexual walls. The quantity of DHEA maintains desired vaginal wall thickness and the integrity of the sexual organs to help prevent prolapses that can occur with age.

Balanced pH levels of the vaginal environment are maintained with the vaginal salve as well. Overgrowth of candida yeast leads to yeast infections that reduces pleasure during sexual activity. The quantity of elderberry extract and the quantity of pomegranate oil aid in pH balance maintenance. The quantity of elderberry extract is an undecylenic acid from the elderberry herb.

In order to maintain hormone levels as well, the quantity of DHEA and the quantity of progesterone counteract high levels of cortisol. High levels of cortisol are typically from chronic stress which affects the overall hormonal health of the body.

The moisture of the vaginal area is necessary not only for sexual activity but for overall vaginal health. The present invention is meant to be used as a weekly moisturizer between sexual encounters to help moisturize the delicate tissue of the vaginal mucosa that often becomes dry as a woman gets older. The present invention also can be used on the vulva area including the vaginal lips and clitoris as these areas become very dry to the point of discomfort as a woman age. The quantity or squalene and the quantity of avocado oil serves to moisturize the vaginal area with the vaginal salve. The quantity of squalene enhances the moisture of the vaginal area that mirrors the moisture naturally produced by the body. The quantity of avocado oil includes Omega fats 3, 6, 7, and 9 that deeply moisturize the skin and mucosal area. Furthermore, the topical application of non-essential fatty acids n-3, n-6, and n-9 heal cutaneous wounds that may result from sexual activity.

The vaginal salve not only enhances sexual pleasure but heals any micro-tears in the vaginal walls that are caused through sexual intercourse. As women age, these micro-tears do not repair as quickly. For younger women, who have sex more often and do not leave a day or two in between, the vaginal salve facilitates the repair of micro-tears to prevent discomfort with more vigorous and more often bouts of sexual activity. The quantity of avocado oil and the quantity of pomegranate oil heal cutaneous wounds in the vaginal area. More specifically, the Omega fats 3, 6, 9 oils in the avocado oil aid repair the micro-tears.

The quantity of avocado oil, the quantity of squalene oil, the quantity of benzoin, the quantity of damiana extract, the quantity of DHEA, the quantity of elderberry extract, the quantity of progesterone, and the quantity of pomegranate oil are incorporated into the vaginal salve with the combination of the quantity of water, the quantity of glycerin, the quantity of cetearyl alcohol, the quantity of glyceryl stearate, the quantity of lecithin, the quantity of xanthan gum, the quantity of citric acid, the quantity of potassium sorbate, and the quantity of sodium benzoate. This combination produces the vaginal salve as a cream that may be topically applied across the vaginal area, both externally and internally. In order for the vaginal salve to be a cream, the quantity of water serves as a solvent, and the quantity of glycerin serves as a humectant. The quantity of cetearyl alcohol, the quantity of lecithin, and the quantity of xanthan gum serve together as an emulsion stabilizer. Moreover, the quantity of lecithin also serves as a skin conditioning agent, and the quantity of glyceryl stearate serves as a lubricant for the skin. Moreover, the quantity of xanthan gum serves as a thickener for the vaginal salve with the quantity of citric acid. The quantity of potassium sorbate serves as a preservative, and the quantity of sodium benzoate serves as a fragrant ingredient.

Figure 3:
FIG. 3 is a continuation of FIG. 2.

As can be seen in FIGS. 2 and 3, in order to properly proportion the vaginal salve that lubricates and promotes blood circulation, the quantity of water is approximately 80.545 percentage by weight (wt. %) of the vaginal salve. The quantity of glycerin is approximately 5.0 wt. % of the vaginal salve. The quantity of cetearyl alcohol is approximately 3.0 wt. % of the vaginal salve. The quantity of glyceryl stearate is approximately 3.0 wt. % of the vaginal salve. The quantity of avocado oil is approximately 2.5 wt. % of the vaginal salve. The quantity of squalene oil is approximately 1.25 wt. % of the vaginal salve. The quantity of lecithin is approximately 1.0 wt. % of the vaginal salve. The quantity of benzoin oil is approximately 1.0 wt. % of the vaginal salve. The quantity of xanthan gum is approximately 0.85 wt. % of the vaginal salve. The quantity of citric acid is approximately 0.4 wt. % of the vaginal salve. The quantity of potassium sorbate is approximately 0.375 wt. % of the vaginal salve. The quantity of DHEA is approximately 0.27 wt. % of the vaginal salve. The quantity of elderberry extract is approximately 0.25 wt. % of the vaginal salve. The quantity of damiana extract is approximately 0.25 wt. % of the vaginal salve. The quantity of progesterone is approximately 0.11 wt. % of the vaginal salve. The quantity of pomegranate oil is approximately 0.1 wt. % of the vaginal salve. The quantity of sodium benzoate is approximately 0.1 wt. % of the vaginal salve. In reference to the aforementioned compositional proportions, the term "approximately" preferably means within an error range of up to ±0.005 wt. %.

The method of use includes the application of the vaginal salve with the vaginal lips and the clitoris, serving as an external vulva moisturizer as needed. The vaginal lips and clitoris can become easily dry and easily irritated and with the application of the vaginal salve a few times a week, moisture is quickly restored to this area. In order for the present invention to be used as an internal vaginal moisturizer, the vaginal salve is internally applied two to three times a week. Dosages may be maintained weekly or bi-weekly as needed. The internal application rejuvenates vaginal walls.

In order for the present invention to be used as a sexual lubricant, approximately 1 gram is applied on a partner before sexual activity.

Although the invention has been explained in relation to its preferred embodiment, it is to be understood that many other possible modifications and variations can be made without departing from the spirit and scope of the invention as hereinafter claimed.

What is claimed is:

1. A composition for restorative vaginal lubrication comprising:
    a quantity of water;
    a quantity of glycerin;
    a quantity of cetearyl alcohol;
    a quantity of glyceryl stearate;
    a quantity of avocado oil;
    a quantity of squalene oil;
    a quantity of lecithin;
    a quantity of benzoin oil;
    a quantity of xanthan gum;
    a quantity of citric acid;
    a quantity of potassium sorbate;
    a quantity of Dehydroepiandrosterone (DHEA);
    a quantity of elderberry extract;
    a quantity of damiana extract;
    a quantity of progesterone;
    a quantity of pomegranate oil;
    a quantity of sodium benzoate; and,
    the quantity of water, the quantity of glycerin, the quantity of cetearyl alcohol, the quantity of glyceryl stearate, the quantity of avocado oil, the quantity of squalene oil, the quantity of lecithin, the quantity of benzoin oil, the quantity of xanthan gum, the quantity of citric acid, the quantity of potassium sorbate, the quantity of DHEA, the quantity of elderberry extract, the quantity of damiana extract, the quantity of progesterone, the quantity of pomegranate oil, and the quantity of sodium benzoate being homogeneously mixed into a vaginal salve.

2. The composition for restorative vaginal lubrication of claim 1 wherein the quantity of water is approximately 80.545 percentage by weight (wt. %) of the vaginal salve.

3. The composition for restorative vaginal lubrication of claim 1 wherein the quantity of glycerin is approximately 5.0 wt. % of the vaginal salve.

4. The composition for restorative vaginal lubrication of claim 1 wherein the quantity of cetearyl alcohol is approximately 3.0 wt. % of the vaginal salve.

5. The composition for restorative vaginal lubrication of claim 1 wherein the quantity of glyceryl stearate is approximately 3.0 wt. % of the vaginal salve.

6. The composition for restorative vaginal lubrication of claim 1, wherein the quantity of avocado oil is approximately 2.5 wt. % of the vaginal salve.

7. The composition for restorative vaginal lubrication of claim 1 wherein the quantity of squalene oil is approximately 1.25 wt. % of the vaginal salve.

8. The composition for restorative vaginal lubrication of claim 1, wherein the quantity of lecithin is approximately 1.0 wt. % of the vaginal salve.

9. The composition for restorative vaginal lubrication of claim 1, wherein the quantity of benzoin oil is approximately 1.0 wt. % of the vaginal salve.

10. The composition for restorative vaginal lubrication of claim 1, wherein the quantity of xanthan gum is approximately 0.85 wt. % of the vaginal salve.

11. The composition for restorative vaginal lubrication of claim 1, wherein the quantity of citric acid is approximately 0.4 wt. % of the vaginal salve.

12. The composition for restorative vaginal lubrication of claim 1, wherein the quantity of potassium sorbate is approximately 0.375 wt. % of the vaginal salve.

13. The composition for restorative vaginal lubrication of claim 1, wherein the quantity of Dehydroepiandrosterone (DHEA) is approximately 0.27 wt. % of the vaginal salve.

14. The composition for restorative vaginal lubrication of claim 1, wherein the quantity of elderberry extract is approximately 0.25 wt. % of the vaginal salve.

15. The composition for restorative vaginal lubrication of claim 1 wherein the quantity of damiana extract is approximately 0.25 wt. % of the vaginal salve.

16. The composition for restorative vaginal lubrication of claim 1, wherein the quantity of progesterone is approximately 0.11 wt. % of the vaginal salve.

17. The composition for restorative vaginal lubrication of claim 1, wherein the quantity of pomegranate oil is approximately 0.1 wt. % of the vaginal salve.

18. The composition for restorative vaginal lubrication of claim 1, wherein the quantity of sodium benzoate is approximately 0.1 wt. % of the vaginal salve.

* * * * *